United States Patent [19]

Bernardi

[11] Patent Number: 4,605,646

[45] Date of Patent: Aug. 12, 1986

[54] COMPOSITIONS BASED ON VEGETABLE FIBRE AND LACTULOSE

[75] Inventor: Roberto Bernardi, Milan, Italy

[73] Assignee: Farmaco Italiano Padil S.r.l., Milan, Italy

[21] Appl. No.: 631,106

[22] Filed: Jul. 16, 1984

[30] Foreign Application Priority Data

Mar. 28, 1984 [IT] Italy .............................. 20257 A/84

[51] Int. Cl.$^4$ ............................................. A61K 31/70
[52] U.S. Cl. ..................................................... 514/53
[58] Field of Search ........................... 424/180; 514/53

[56] References Cited

U.S. PATENT DOCUMENTS 3,867,524  2/1975  Ebner ................................... 424/180
4,198,400  4/1980  Biegler ................................ 424/180

Primary Examiner—Johnnie R. Brown
Assistant Examiner—Elli Peselev
Attorney, Agent, or Firm—Stevens, Davis, Miller & Mosher

[57] ABSTRACT

Compositions of therapeutic or dietetic use have been prepared comprising vegetable fibre and lactulose. The two components have demonstrated a strong reciprocal synergic effect, by which with compositions which provide a daily quantity of 0.5–2.5 g of raw fibre and 5–10 g of lactulose it is possible to obtain therapeutic effects on the gastrointestinal system which are better than those obtainable by a daily administration of 10–20 g of raw fibre or 10–20 g of lactulose.

6 Claims, No Drawings

COMPOSITIONS BASED ON VEGETABLE FIBRE AND LACTULOSE

This invention relates to new compositions of therapeutic and dietetic activity, essentially constituted by vegetable fibre and lactulose.

In relatively recent years, research of an epidemiological character has shown that if the human body consumes an adequate quantity of vegetable fibre, a considerable improvement in intestine functioning is observed, in particular with regard to the normal transit and rhythmic evacuation of the alvus.

Simultaneously, many hundreds of practiced gastroenterologists have carried out clinical trials which have progressively shown the usefulness of a high administration of fibre in opposing very frequent pathological conditions such as an irritable colon, diverticulosis and other analogous conditions. More importantly, it has been found that fibre interferes with the absorption of bile salts, which seems to determine the prevention of cholecystic calculus formation, thus controlling possible hypercholesterolemia states.

These latter observations probably require further more extensive confirmation, but give some reason for the enormous interest which doctors and dieteticians assign to vegetable fibre in human feeding.

In all cases, the experimentors in this field agree in maintaining that in order to obtain the benefits of vegetable fibre ingestion, and in particular the desired improvement in intestine functioning, a supplementary fibre quantity of at least 10-20 grams per day over a normal diet is necessary.

In order to provide said supplementary fibre quantity, various preparations have been produced and are commercially available, ranging from simple bran administered with spoons, to tablets to be swallowed, and sweetmeats.

However, none of the commercial preparations allows regular administration of the necessary fibre quantity, either because of the poor product organoleptic qualities or because they are poorly accepted by the patient, or again because they require the administration of other substances (such as sugar) which in most of the subjects treated are contraindicated because of their high calorific value.

It should be noted that vegetable fibre or dietetic fibre can be obtained from any food product of vegetable origin such as cereals (wheat, maize, barley etc.), roots (potatoes and the like), leaf vegetables and fruit, and is constituted essentially by polysaccharides (cellulose, hemicellulose, lignin, pectin) which are not assimilated in the small intestine, and instead ferment in the colon, which they reach practically unaltered.

Dietetic fibre, in the state in which it is obtained from various processes, contains between 11 and 22% of fibre which is actually useful of therapeutic purposes. This fibre, ie "active" fibre, is known as "raw fibre".

These terms, defined in this manner, will be referred to hereinafter.

In addition, there has been commercially available for about ten years a disaccharide known as lactulose, which is not present as such in nature, but is prepared synthetically by treating natural substances.

Lactulose is widely used, in the form of either 50% syrup or crystalline product, as a medicine for the treatment of chronic constipation.

The commonly accepted therapeutic dose is around 20 g/day of active substance.

The activity of lactulose seems to depend on the fact that the gastroenteric system of man lacks specific enzymes (disaccharidase) able to split it, and thus it reaches the colon intact with the result that only at this point is the physiologically present bacterial flora able to exert a breaking-down action on the disaccharide molecule. A large quantity of short-chain acids is released, which considerably acidifies the intestinal environment, and at the same time, by means of an osmotic mechanism, water is strongly drawn from the intestinal walls towards the intestinal lumen itself. By virtue of this basic mechanism and a subsequent modification of the intestinal flora, a simultaneous laxative effect is produced, which facilitates elimination of ammonia and other toxic substances, and also reduces their production.

In essence, lactulose produces effects analogous to those of dietetic fibre, but by means of completely different mechanisms.

We have now surprisingly discovered that compositions containing vegetable fibre and lactulose in association enable therapeutic results to be obtained which are decidedly better that those obtainable by the components alone, and using doses of each which are 2-3 times less than those normally used, this forming the subject matter of the present invention.

In other words it has been unexpectedly found that there is a considerable synergistic effect between vegetable fibre and lactulose to the extent that it is possible to obtain an excellent activation of the physiological motility of the last portions of the intestine together with a reduced production and diminished absorption of certain toxic substances, by administering compositions containing vegetable fibre and lactulose diluted in suitable excipients or edible substances such that the daily administration is 0.5-2.5 g of raw fibre and 5-10 g of lactulose.

It is immediately apparent that a daily administration of 0.7-2 g of raw fibre is much more tolerable than an administration of 10-20 g, which requires the consumption of 100-400 g of dietetic fibre.

Moreover, as the lactulose has considerable sweetening power it makes the fibre more acceptable to the taste, while at the same time maintaining the calorie-free concept, very important in certain cases, by virtue of the fact that the lactulose is not assimilated.

The new compositions are also highly advantageous when compared with the administration of lactulose alone. In this case, an administration of ½ and, more frequently, ¼ of the normal therapeutic dose is much more easily accepted, both because at such doses any side-effect of the lactulose disappears, and because the therapeutic effect of the new compositions is actually qualitatively better.

It has also been found, and constitutes a specific subject matter of the present invention, that the new compositions can be conveniently produced in the form of dietetic products, in particular in the form of biscuits possessing excellent organoleptic characteristics, and particularly suitable for breakfast.

In such a case, the vegetable fibre can be advantageously provided by materials such as wheat meal, oat meal, corn flour and the like, all of which are materials which do not require substances of high calorific value to be administered together with the fibre.

Alternatively, tablets or pills of more obvious pharmaceutical use can be prepared from the vegetable fibre and lactulose.

Hundreds of clinical trials have been carried out with the new compositions according to the invention.

The results obtained in two of these trials are described schematically hereinafter to represent a pure illustration of the invention, and in no way limitative thereof.

In particular, the clinical trials summarised hereinafter specifically illustrate the laxative therapeutic effect, but it is apparent that the claimed compositions retain and improve all the therapeutic characteristics of vegetable fibre and lactulose within the range of the doses described and claimed.

EXAMPLE 1

This experiment was carried out on 10 subjects suffering from chronic constipation complicated by intolerance or reduced sensitivity to laxatives of various types, the experiment being carried out after a period of observation without treatment.

Two groups were formed, each comprising 5 subjects.

The 1st group was treated for a period of one month with a composition (A) constituted by:

|  | kg | % |
| --- | --- | --- |
| Flour type 0 (0.7% fibre) | 1.300 | 36.50 |
| 50% lactulose | 0.750 | 21.00 |
| Soft wheat bran (11% fibre) | 0.900 | 25.30 |
| Vegetable margarine | 0.300 | 8.50 |
| Corn starch | 0.150 | 2.80 |
| Powdered skimmed milk | 0.100 | 4.20 |
| Ammonium bicarbonate | 0.030 | 0.85 |
| Soy lecithin | 0.030 | 0.85 |
| Natural flavours | as required | |
| Salt | as required | |
|  | 3.560 | 100 |

After suitable processing, the composition was administered so as to provide each subject with a daily quantity of 1.3 g of raw fibre and 10 g of lactulose.

After 5 days of rest, the same group of subjects was treated for one month with a composition (B) constituted by 50% lactulose syrup, such that each subject received a daily quantity of 20 g of lactulose.

The 2nd group of 5 subjects was treated in the reverse manner, for the first month with composition (B), and after 5 days of rest, for a further month with composition (A).

The experiment was carried out by requiring all subjects to adopt their normal diet and to follow their normal rhythm of life. A systematic observation was made of the number of daily and weekly evacuations, the characteristics of the feces, the appearance of general or intestinal symptoms, and any variations in the symptoms previously or habitually complained of by the individual subjects. At the end of the experiment, the subjects were carefully questioned with regard to any differences which they had noted during the course of the two treatments, and in particular with regard to the enjoyment of the treatments themselves.

The results of the experiments lead to the following observations.

Eight patients out of ten stated that they had obtained an evacuating effect from treatment (A) which in terms of regularity, quality and quantity of the individual evacuations, was more satisfactory both than normal behaviour and than treatment (B).

Only occasionally were semi-liquid feces emitted.

With treatment (B), six subjects noted frequent emission of feces having a consistency variable from semi-liquid to liquid, resulting in some consequent problem.

They were consequently induced to reduce the dosage, with consequent reduction of the evacuating effects to unsatisfactory levels.

Two subjects interrupted the administration of treatment (B) because moderate but evident gastrointestinal disturbances arose.

A further two subjects, even though continuously undergoing treatment (B) at full dosage, noted an insufficient and con-constant laxative effect.

The experiment thus demonstrated overall that associating a small quantity of fibre with lactulose enables a more constant, uniform and satisfactory evacuating effect to be obtained than with a double dose of lactulose alone.

In addition, the subjects in all cases found treatment (A) more pleasing to undergo. Taking preparation (A) in the form of biscuits for breakfast or, more rarely, during the day, was judged to be pleasant and practical.

The favourable judgement was aided by the impression of "not taking a medicine" but instead taking a simple dietetic food.

EXAMPLE 2

14 subjects suffering from chronic constipation complicated by various symptoms of suffering of the large intestine underwent the comparative treatment. They were divided on the basis of a randomisation criterion into two groups of 7 subjects, suitably equivalent in terms of their various characteristics (age, sex, duration of the disturbance, living habits etc.).

The 1st group took for breakfast only 50 g of biscuits containing 5% of vegetable fibre (2.5 g/day of raw fibre) and 10% of lactulose (5 g/day of lactulose) for one month.

The 2nd group took cereal flakes containing a high fibre percentage for breakfast, so as to provide 5-10 g/day of raw fibre, according to availability and tolerance, for one month.

In all cases, the laxative effect was more rapid, more constant and more intense in the first group. A considerable reduction in other colic symptoms was also noted.

In the 2nd group, the laxative effect was considered satisfactory only in two subjects. Two subjects did not continue the treatment for the entire established period because of intolerance. The remaining subjects cosidered the laxative effect insufficient.

This test therefore showed that the vegetable fibre-lactulose association provides a more intense, uniform and satisfactory laxative effect than a fibre quantity which is two, three or more times greater. The difficulty in continuously taking the set fibre doses in the form of cereal flakes did not compromise the correctness of the experiment, but instead demonstrated the greater acceptance of the fibre-lactulose biscuits.

I claim:

1. A laxative composition comprising 5-10 grams of lactulose per 0.5-2.5 grams of raw fibre, and an inert excipient.

2. A laxative composition comprising lactulose and raw fibre in a weight ratio of 2:1 to 20:1 and an inert excipient.

3. The laxative composition as recited in claim 2 in the form of a low calorie dietetic product.

4. The laxative composition as recited in claim 3 in the form of biscuits.

5. The laxative composition as recited in claim 2 in the form of pills or tablets.

6. A method for treating constipation which comprises administering to a patient daily 5 to 10 grams of lactualose and from 0.5 to 2.5 grams of raw fibre.

* * * * *